United States Patent
Chou et al.

(10) Patent No.: US 7,560,559 B2
(45) Date of Patent: Jul. 14, 2009

(54) POLYMORPHIC FORM OF MONTELUKAST SODIUM

(75) Inventors: Jun-Hong Chou, Blue Bell, PA (US);
Michael B. Gentzler, Wayne, PA (US);
James N. Michaels, Perkasie, PA (US);
Cynthia Bazin, Saint-Hubert (CA);
Sophie-Dorothee Clas, Montreal (CA);
Chad Dalton, St-Lazare (CA); Michael Guojie Wu, Edison, NJ (US)

(73) Assignees: Merck & Co., Inc., Rahway, NJ (US);
Merck Frosst Canada & Co., Quebec (CA)

( * ) Notice: Subject to any disclaimer, the term of this patent is extended or adjusted under 35 U.S.C. 154(b) by 584 days.

(21) Appl. No.: 10/553,069

(22) PCT Filed: Apr. 12, 2004

(86) PCT No.: PCT/US2004/011211

§ 371 (c)(1),
(2), (4) Date: Oct. 12, 2005

(87) PCT Pub. No.: WO2004/091618

PCT Pub. Date: Oct. 28, 2004

(65) Prior Publication Data

US 2006/0194838 A1    Aug. 31, 2006

Related U.S. Application Data

(60) Provisional application No. 60/462,941, filed on Apr. 15, 2003.

(51) Int. Cl.
*C07D 215/38*     (2006.01)
*A61K 31/44*      (2006.01)

(52) U.S. Cl. .................. 546/171; 514/311; 514/313
(58) Field of Classification Search ................. 546/171; 514/311, 313
See application file for complete search history.

(56) References Cited

U.S. PATENT DOCUMENTS

| | | | | |
|---|---|---|---|---|
| 5,565,473 A | * | 10/1996 | Belley et al. | ................. 514/313 |
| 5,614,632 A | | 3/1997 | Bhupathy et al. | |
| 5,869,673 A | * | 2/1999 | Tung et al. | ................... 546/172 |
| 5,952,347 A | * | 9/1999 | Arison et al. | ................ 514/311 |
| 6,320,052 B1 | | 11/2001 | Bhupathy et al. | |

OTHER PUBLICATIONS

Elliott Israel, MD, et al., *Effects of Montelukast and Beclomethasone on Airway Function and Asthma Control*, J. Allergy Clin. Immunol., vol. 110, pp. 847-854, Dec. 2002.

Chester J. Kitchen, et al., *A Semi-Automated 96-Well Protein Precipitation Method for the Determination of Montelukast in Human Plasma Using High Performance Liquid Chromatography/Fluoroescence Detection*, J. Pharm. Biomed. Anal., vol. 31, pp. 647-654, Jan. 2003.

* cited by examiner

*Primary Examiner*—D. Margaret Seaman
(74) *Attorney, Agent, or Firm*—Mollie M. Yang; Valerie J. Camara

(57) ABSTRACT

The invention provides novel polymorphic form of montelukast sodium, as well as methods of using and pharmaceutical compositions containing saud novel form. Also provided are montelukast sodium: acetonitrile solvates, which are intermediates in the formation of crystalline montelukast sodium.

10 Claims, 3 Drawing Sheets

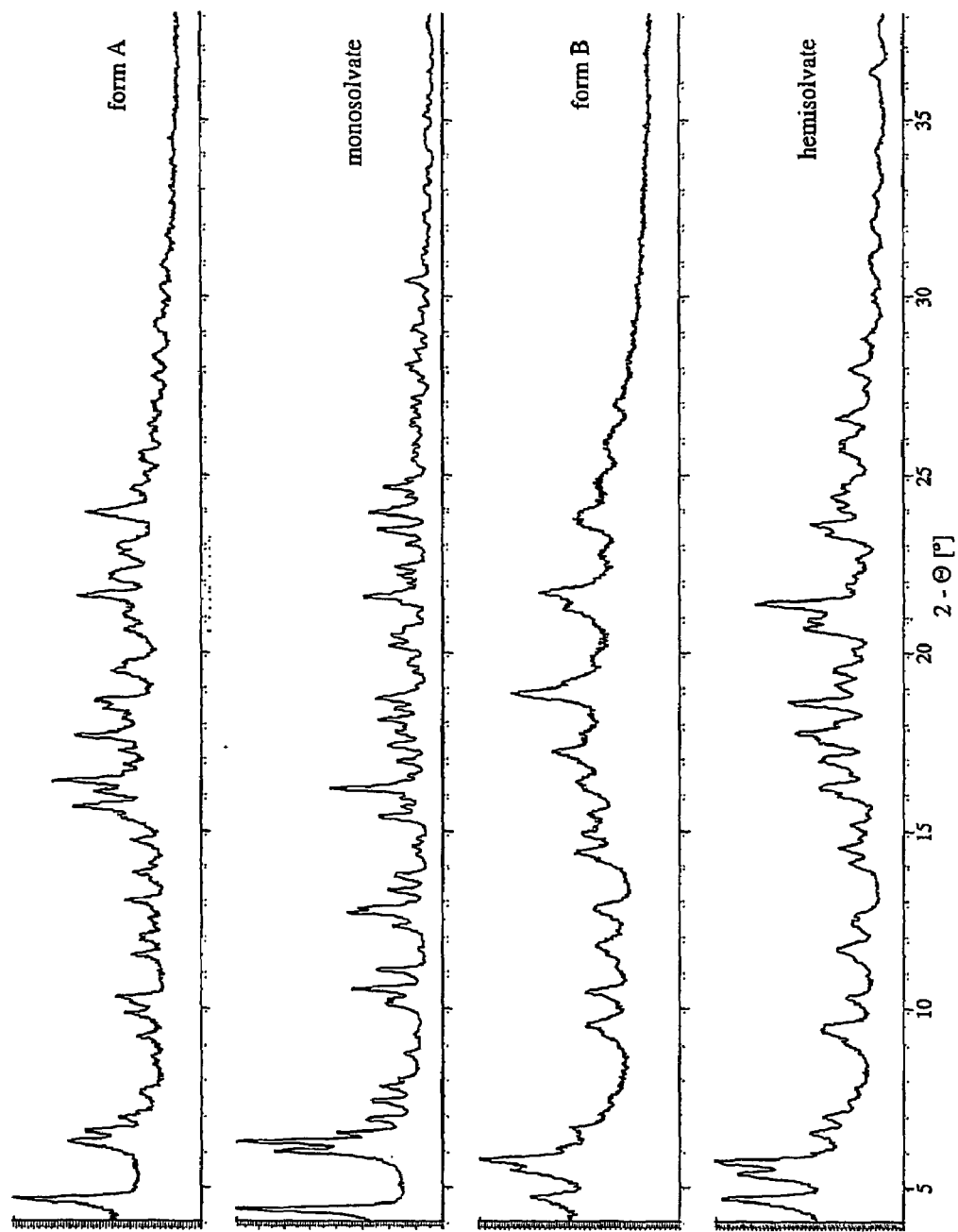
FIG. 1 Powder x-ray diffraction patterns for montelukast sodium Form A, monosolvate, form B, and hemisolvate.

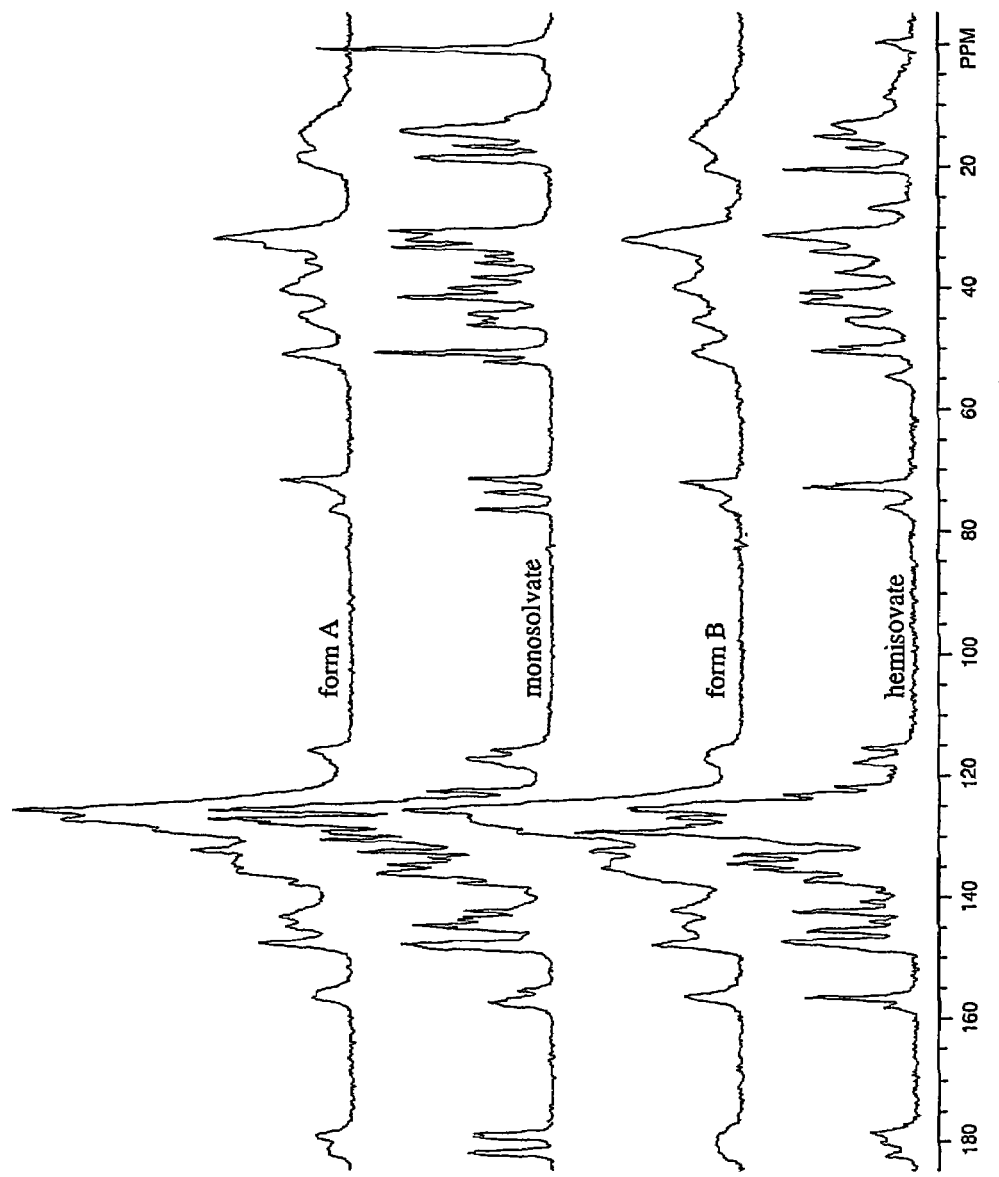
FIG. 2 $^1H$-$^{13}C$ CPMAS room-temperature NMR spectra of montelukast sodium form A, form B, monosolvate, hemisolvate.

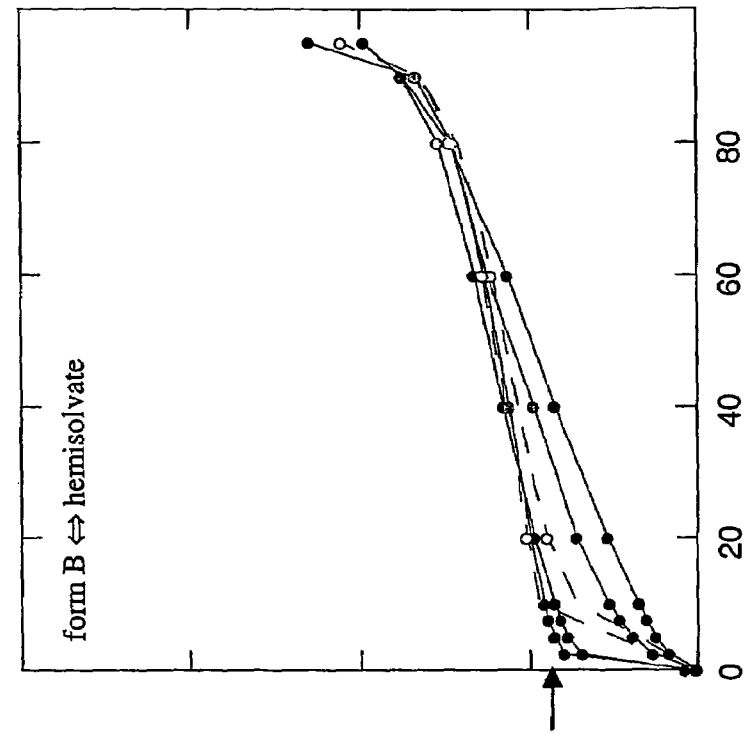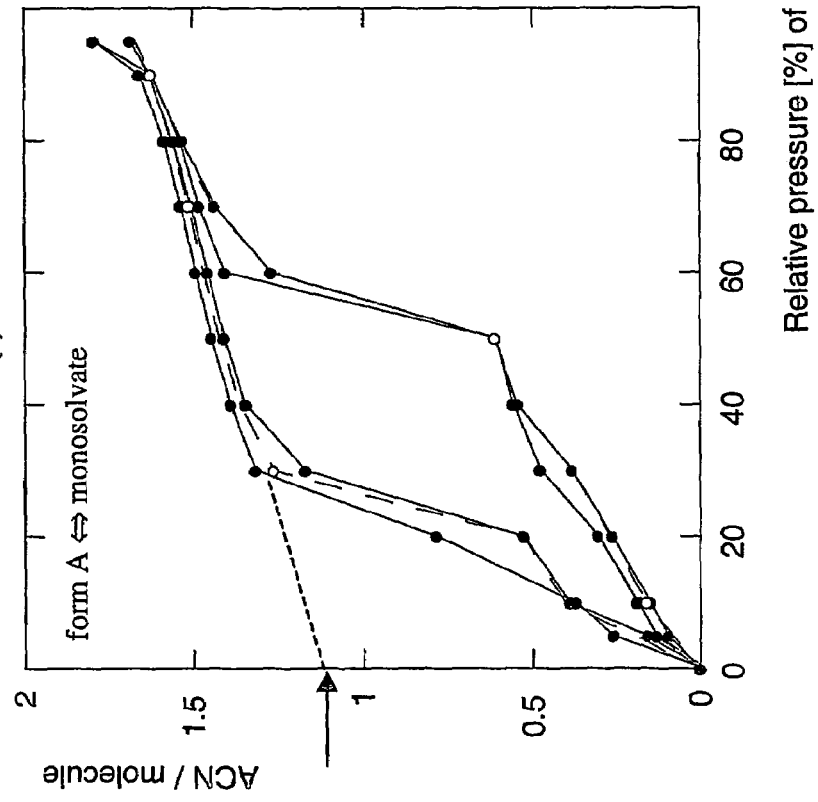
FIG. 3 CH3CN sorption isotherms of montelukast form A [3(a)] and form B [3(b)]. (This statement is not shown in drawing submitted: Red circles were drawn as triangles in the application paper)

POLYMORPHIC FORM OF MONTELUKAST SODIUM

CROSS REFERENCE TO RELATED APPLICATIONS

This application is the National Stage of International Application No. PCT/US04/11211, filed 12 Apr. 2004, which claims the benefit under 35 U.S.C. 119(e) of U.S. Provisional Application No. 60/462,941, filed 15 Apr. 2003.

BACKGROUND OF THE INVENTION

Montelukast sodium is the active pharmaceutical ingredient of SINGULAIR®, and is approved for the treatment of asthma and allergic rhinitis. The molecular structure of montelukast is as shown below:

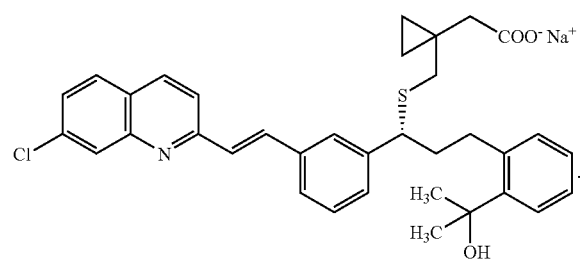

Montelukast sodium is described in U.S. Pat. No. 5,565,473. A crystalline form of montelukast sodium (hereinafter referred to as "Form A") is described in U.S. Pat. No. 5,614,632.

SUMMARY OF THE INVENTION

The present invention provides for a new crystalline form of montelukast sodium, process for its preparation, its use in the manufacture of medicaments, as well as novel montelukast sodium:acetonitrile solvates.

BRIEF DESCRIPTION OF THE DRAWINGS

FIG. 1 shows X-ray powder diffraction patterns for montelukast sodium Form A, montelukast sodium Form B, montelukast sodium:acetonitrile monosolvate, and montelukast sodium:acetonitrile hemisolvate.

FIG. 2 shows $^{13}C$ CPMAS NMR spectra of montelukast sodium Form A, montelukast sodium Form B, montelukast sodium: acetonitrile monosolvate, and montelukast sodium: acetonitrile hemisolvate.

FIG. 3 shows $CH_3CN$ sorption isotherms of montelukast form A (FIG. 3(a)) and Form B (FIG. 3(b)) as a function of $CH_3CN$ partial pressure in nitrogen. Measurements at 20° C. [circle] and 40° C. [triangle] are shown. The sorbed $CH_3CN$ mass has been converted to a molar ratio, and the extrapolation to solvate content is shown.

DETAILED DESCRIPTION OF THE INVENTION

In one aspect of the present invention there is provided a novel crystalline polymorph (hereinafter referred to as "Form B") of montelukast sodium, which is characterized by the following X-ray powder diffraction peak positions (vs=very strong, s=strong, m=moderate, w=weak); the peaks for Form A are shown for comparison:

| Form B | | | Form A | | |
|---|---|---|---|---|---|
| 2 θ | d spacing (A) | Intensity | 2 θ | d spacing (A) | Intensity |
| 4.62 | 19.1 | s | 4.60 | 19.2 | vs |
| 5.4 | 16.4 | s | 6.2 | 14.2 | m |
| 5.7 | 15.6 | vs | 6.5 | 13.5 | m |
| 6.6 | 13.5 | m | 6.9 | 12.7 | w |
| 9.5 | 9.3 | m | 9.8 | 9.0 | w |
| 10.4 | 8.5 | m | 10.2 | 8.6 | w |
| 11.7 | 7.6 | w | 13.1 | 6.8 | w |
| 12.8 | 6.9 | w | 15.7 | 5.6 | s |
| 14.3 | 6.2 | m | 16.4 | 5.4 | m |
| 14.8 | 6.0 | m | 17.7 | 5.0 | m |
| 15.4 | 5.7 | w | 18.6 | 4.78 | m |
| 17.1 | 5.2 | s | 19.7 | 4.50 | w |
| 18.7 | 4.73 | s | 21.6 | 4.12 | m |
| 21.6 | 4.11 | s | 23.9 | 3.71 | m |
| 23.8 | 3.74 | m | | | |

In particular, the peaks at 2θ=5.4, 5.7, 9.5, 10.4, 17.1, 18.7, and, 21.6 are unique to Form B. Representative X-ray powder diffraction patterns and $^{13}C$ solid state NMR spectra for Form A and From B are shown in FIGS. 1 and 2, respectively.

In another aspect the present invention provides a pharmaceutical composition which comprises a therapeutically effective amount of Form B montelukast sodium and a pharmaceutically acceptable carrier.

In a third aspect the present invention provides a method for the preparation of crystalline montelukast sodium Form B which comprises converting montelukast sodium:acetonitrile monosolvate to montelukast sodium:acetonitrile hemisolvate, and removing acetonitrile from said hemisolvate to provide montelukast sodium Form B.

In a fourth aspect the present invention provides for the use of montelukast sodium Form B in the manufacture of medicaments for the treatment of leukotriene-mediated conditions.

In a fifth aspect the present invention provides a method for the preparation of montelukast sodium Form A, substantially free of amorphous montelukast sodium, which comprises 1) collecting montelukast sodium:acetonitrile monosolvate; and 2) removing acetonitrile from montelukast sodium:acetonitrile monosolvate to provide said montelukast sodium Form A substantially free of amorphous montelukast sodium.

In a sixth aspect the present invention provides novel crystalline acetonitrile solvates of montelukast sodium selected from montelukast sodium:acetonitrile monosolvate [1:1 acetonitrile:montelukast sodium molar ratio] and montelukast sodium:acetonitrile hemisolvate [2:1 acetonitrile:montelukast sodium molar ratio], wherein the monosolvate and the hemisolvate are characterized by $^{13}C$ solid state NMR and X-ray powder diffraction peak positions given below. Representative X-ray powder diffraction patterns and $^{13}C$ solid state NMR spectra of the monosolvate and hemisolvate are shown in FIGS. 1 and 2, respectively.

| $^{13}$C solid-state CPMAS NMR: | | | |
| --- | --- | --- | --- |
| Hemisolvate | | Monosolvate | |
| ppm* | comment** | ppm* | comment** |
| 0 | acetonitrile | 1 | acetonitrile |
| 27 | well-resolved | 72, 74, 77 | sharp triplet |
| 55 | well-resolved | 179, 182 | sharp doublet |

*isotropic chemical shifts in ppm, rounded (+/−0.5 ppm) and referenced by setting the carbonyl resonance of glycine to 176.08 ppm.
**acetonitrile peaks indicate solvate crystal form; the remaining peaks are resonances that are either relatively well-resolved (from peaks in spectra of other forms) or that have a multiplet appearance that is distinct (relative to that of other forms)-as observed under conditions described in Characterization of montelukast sodium polymorphs and solvates.

X-ray Powder Diffraction:

| Hemisolvate | | | Monosolvate | | |
| --- | --- | --- | --- | --- | --- |
| 2 θ | d spacing (Å) | Intensity | 2 θ | d spacing (Å) | Intensity |
| 4.57 | 19.3 | s | 4.30 | 20.5 | vs |
| 5.3 | 16.7 | s | 5.9 | 14.9 | s |
| 5.6 | 15.7 | vs | 6.2 | 14.3 | s |
| 6.5 | 13.6 | m | 6.8 | 13.0 | w |
| 9.4 | 9.4 | m | 7.3 | 12.0 | w |
| 10.3 | 8.6 | w | 10.5 | 8.4 | m |
| 11.6 | 7.6 | m | 11.0 | 8.0 | w |
| 14.1 | 6.3 | w | 12.7 | 7.0 | m |
| 14.5 | 6.1 | m | 16.2 | 5.5 | s |
| 15.1 | 5.8 | w | 18.1 | 4.90 | w |
| 16.2 | 5.5 | m | 18.7 | 4.74 | w |
| 17.0 | 5.2 | m | 21.6 | 4.12 | w |
| 18.5 | 4.79 | s | 23.4 | 3.80 | w |
| 20.8 | 4.26 | m | 23.9 | 3.72 | w |
| 21.3 | 4.17 | s | | | |

Montelukast sodium Form B has the same utility as the Form A material, and may be used for the treatment and prevention of leukotriene-mediated diseases and disorders in the same manner as the Form A material. Leukotriene antagonists such as montelukast are useful in the treatment of asthma, allergic rhinitis (including seasonal and perennial), atopic dermatitis, chronic urticaria, sinusitis, nasal polyps, chronic obstructive pulmonary disease, conjunctivitis including rhinoconjunctivitis, migraine, cystic fibrosis, and wheezing secondary to viral (such as respiratory syncytial virus) bronchiolitis, among others.

For the treatment of asthma, montelukast sodium Form B may be administered to patients in accordance with the established dose of about 10 mg per day for adult, and from about 2 to about 5 mg per day for children. The magnitude of the dose may, however, vary with the nature and the severity of the condition to be treated, and the age, weight and response of the individual patient; a physician of ordinary skill in the art will be able to adjust the typical dose upward or downward to devise a suitable dose and dosing schedule based on the individual characteristics and need of the patient.

For the treatment of allergic rhinitis (including seasonal and perennial), montelukast sodium Form B may be administered in accordance with the established dose of about 10 mg per day for adult, and from about 2 to about 5 mg per day for children. The magnitude of the dose may, however, vary with the nature and the severity of the condition to be treated, and the age, weight and response of the individual patient; a physician of ordinary skill in the art will be able to adjust the typical dose upward or downward to devise a suitable dose and dosing schedule based on the individual characteristics and need of the patient.

For the treatment of atopic dermatitis, montelukast sodium Form B may be administered to patients at a dose of about 10 mg per day for adult, and from about 2 to about 5 mg per day for children. The magnitude of the dose may, however, vary with the nature and the severity of the condition to be treated, and the age, weight and response of the individual patient; a physician of ordinary skill in the art will be able to adjust the typical dose upward or downward to devise a suitable dose and dosing schedule based on the individual characteristics and need of the patient.

For the treatment of chronic urticaria, montelukast sodium Form B may be administered to patients at a dose of about 10 mg per day for adult, and from about 2 to about 5 mg per day for children. The magnitude of the dose may, however, vary with the nature and the severity of the condition to be treated, and the age, weight and response of the individual patient; a physician of ordinary skill in the art will be able to adjust the typical dose upward or downward to devise a suitable dose and dosing schedule based on the individual characteristics and need of the patient.

For the treatment of sinusitis, montelukast sodium Form B may be administered administered to patients at a dose of about 10 mg per day for adult, and from about 2 to about 5 mg per day for children. The magnitude of the dose may, however, vary with the nature and the severity of the condition to be treated, and the age, weight and response of the individual patient; a physician of ordinary skill in the art will be able to adjust the typical dose upward or downward to devise a suitable dose and dosing schedule based on the individual characteristics and need of the patient.

For the treatment of nasal polyps, montelukast sodium Form B may be administered administered to patients at a dose of about 10 mg per day for adult, and from about 2 to about 5 mg per day for children. The magnitude of the dose may, however, vary with the nature and the severity of the condition to be treated, and the age, weight and response of the individual patient; a physician of ordinary skill in the art will be able to adjust the typical dose upward or downward to devise a suitable dose and dosing schedule based on the individual characteristics and need of the patient.

For the treatment of chronic obstructive pulmonary disease (COPD), montelukast sodium Form B may be administered to patients at a dose of about 10 mg per day for adult, and from about 2 to about 5 mg per day for children. The magnitude of the dose may, however, vary with the nature and the severity of the condition to be treated, and the age, weight and response of the individual patient; a physician of ordinary skill in the art will be able to adjust the typical dose upward or downward to devise a suitable dose and dosing schedule based on the individual characteristics and need of the patient.

For the treatment of conjunctivitis (including rhinoconjunctivitis), montelukast sodium Form B may be administered to patients at a dose of about 10 mg per day for adult, and from about 2 to about 5 mg per day for children. The magnitude of the dose may, however, vary with the nature and the severity of the condition to be treated, and the age, weight and response of the individual patient; a physician of ordinary skill in the art will be able to adjust the typical dose upward or downward to devise a suitable dose and dosing schedule based on the individual characteristics and need of the patient.

For the treatment of cystic fibrosis, montelukast sodium Form B may be administered to patients at a dose of about 10 mg per day for adult, and from about 2 to about 5 mg per day for children. The magnitude of the dose may, however, vary with the nature and the severity of the condition to be treated, and the age, weight and response of the individual patient; a physician of ordinary skill in the art will be able to adjust the typical dose upward or downward to devise a suitable dose and dosing schedule based on the individual characteristics and need of the patient.

For the treatment of wheezy kid syndrome, or respiratory symptoms associated with viral (such as respiratory syncytial virus) bronchiolitis, montelukast sodium Form B may be administered to patients at a dose of about 10 mg per day for adult, and from about 2 to about 5 mg per day for children. The magnitude of the dose may, however, vary with the nature and the severity of the condition to be treated, and the age, weight and response of the individual patient; a physician of ordinary skill in the art will be able to adjust the typical dose upward or downward to devise a suitable dose and dosing schedule based on the individual characteristics and need of the patient.

Montelukast sodium Form B may be used in the preparation of pharmaceutical products for use in the treatment of leukotriene-mediated diseases such as those described above. Any suitable route of administration may be employed for providing a mammal, especially a human with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, nasal spray and the like. The preferred route of administration for montelukast sodium is by oral administration, for example using tablet, capsule or oral granules formulations.

The compositions include compositions suitable for oral, rectal, topical, parenteral (including subcutaneous, intramuscular, and intravenous), ocular (ophthalmic), pulmonary (nasal or buccal inhalation), or intranasal administration, although the most suitable route in any given case will depend on the nature and severity of the conditions being treated and on the nature of the active ingredient. They may be conveniently presented in unit dosage form and prepared by any of the methods well-known in the art of pharmacy.

Montelukast sodium Form B may be used for the preparation of inhalation compositions such as aerosol spray presentation from pressurized packs or nebulisers, or powders which may be formulated and the powder composition may be inhaled with the aid of an insufflation powder inhaler device. The preferred delivery system for inhalation is a metered dose inhalation (MDI) aerosol, which may be formulated as a suspension or solution of the active ingredient in suitable propellants, such as fluorocarbons or hydrocarbons, or a dry powder inhaler device.

Montelukast sodium Form B may be used for the preparation of topical compositions such as in transdermal devices, aerosols, creams, ointments, lotions, dusting powders, nasal spray and the like in accordance with conventional pharmaceutical formulation practices well known in the art.

In practical use, montelukast Form B can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, capsules and tablets, with the solid oral preparations being preferred over the liquid preparations. Because of their ease of administration, tablets and capsules represent the most advantageous oral dosage unit form in which case solid pharmaceutical carriers are obviously employed. If desired, tablets may be coated by standard aqueous or nonaqueous techniques.

Pharmaceutical compositions of the present invention suitable for oral administration may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each tablet contains from about 2.5 mg to about 20 mg of the active ingredient and each cachet or capsule contains from about 2.5 to about 20 mg of the active ingredient.

Montelukast sodium Form B is obtained from montelukast sodium:acetonitrile hemisolvate via montelukast sodium:acetonitrile monosolvate. The monosolvate may be produced by contacting montelukast sodium in solution, in solid amorphous form, in Form A, or any combinations thereof, with acetonitrile with little to no stirring or agitation. Thus, placing amorphous montelukast sodium or a mixture of amorphous and Form A montelukast sodium into liquid acetonitrile with no or limited stirring or agitation provides montelukast sodium:acetonitrile monosolvate. The conversion may be carried out at any temperature conducive to product formation, for example from ambient temperature to about 80° C., a subset of which is from about 55 to about 75° C. In another method, Form A exposed at room or elevated temperature to acetonitrile vapor at 30% or more of its saturation pressure results in crystalline montelukast sodium:acetonitrile monosolvate. In the preparation of montelukast sodium Form B, montelukast sodium:acetonitrile monosolvate may be generated in situ using procedures described above, and, without being isolated, directly converted the hemisolvate.

The hemisolvate is produced by stirring or otherwise agitating the monosolvate (either isolated or generated in situ) in liquid acetonitrile at a temperature conducive to product formation, for example from ambient temperature to about 80° C. or from about 25 to about 75° C. The hemisolvate may be collected by filtration. Removing acetonitrile from montelukast sodium:acetonitrile hemisolvate, for example by drying such as drying in air at room temperature, provides montelukast sodium Form B. Form B may be converted back to the hemisolvate upon exposure to acetonitrile liquid or acetonitrile vapor at 5% or more of its saturation pressure.

The present invention also provides a process for producing montelukast sodium Form A that is substantially free of amorphous montelukast sodium which comprises collecting montelukast:acetonitrile monosolvate, and removing the acetonitrile from the monosolvate to provide montelukast sodium Form A substantially free of amorphous material.

Thus, montelukast sodium (amorphous or a combination of amorphous and Form A) in acetonitrile is briefly agitated to disperse the solid, for example by stirring for one hour or less. The monosolvate formed is collected, and removing the acetonitrile, for example by drying such as drying in air at room temperature, provides montelukast sodium Form A that is substantially free of amorphous montelukast sodium. The Form A obtained from drying the monosolvate shows melting enthalpies of 29 (+/−2) J/g.

Characterization of Montelukast Sodium Polymorphs and Solvates

The polymorphs Form A and Form B of montelukast sodium, as well as montelukast sodium acetonitrile monosolvate and hemisolvate, were characteriazed using the following methodologies:

(a) Environmental Scanning Electron Microscopy (ESEM)

Samples were examined in a Phillips-Electroscan 2010 ESEM. Montelukast sodium powder was affixed to a standard aluminum stub using double-sided carbon tape. Samples were gold-coated in air with an SPI-Module Sputter Coater for 10 s at 18 mA (chamber pressure, 2 mbar). Imaging was performed with the following conditions: beam voltage=15 kV; filament current=1.75 mA; emission current=39 µA; working distance=7-14 mm; and chamber pressure=3.5-5.0 torr.

Both forms had a needle morphology. At higher magnification, the Form A needles appeared to be thicker and more rigid than those of Form B.

(b) Powder X-ray Diffraction (XRD)

Powder XRD patterns were collected with a Bruker-Siemens D5000 diffractometer equipped with parallel beam optics and Anton-Paar TTK stage. Samples were loosely packed into standard Cr/Cu sample holders and smoothed with a glass slide. Patterns were collected using the following parameters: tube voltage=40 KV; tube current=40 mA; locked-couple scan; 2θ range=4-40°; step size=0.02°; and step time=10 s.

Representative powder x-ray diffraction patterns for the four forms are shown in FIG. 1. All four patterns are distinct. The positions of select peaks for the four forms are presented hereinabove.

(c) Nuclear Magnetic Resonance

Solid-state room-temperature MAS NMR spectra were acquired with a narrow-bore magnet, supersonic Doty probe and a Varian Unity spectrometer operating at 50.28 MHz for $^{13}$C and 52.89 MHz for 23Na. Samples were packed in 4-mm zirconia or SiN rotors with Kel-F caps. The magic angle was set with KBr and $^1$H frequency optimized with glycine. MAS spinning speed was actively controlled to within 5 Hz.

$^1$H-$^{13}$C CPMAS spectra were acquired for high-crystallinity montelukast samples. All spectra were referenced by setting the glycine carbonyl to 176.08 ppm. Processing included $1^{st}$ order phase correction and no apodization. Parameters: recycle delay=3 seconds, contact time=2 ms, MAS speed=7200 Hz, $^1$H 90°=3.7 µs, CP power=67 kHz, decoupling=125 kHz, sweep width=25 kHz, scans=4096-8192, acquisition time=50 ms.

FIG. 2 shows representative $^{13}$C solid-state NMR CPMAS spectra for the four forms. The patterns are all distinct; however, only the solvates spectra have the relative narrow lines that are expected for crystal forms with excellent conformational order. The peak near 0 to 1 ppm for the solvates is acetonitrile. The hemisolvate shows peaks at 27 and 55 ppm that are well-resolved from spectra of the other forms. All spectra show peaks with multiple resonances per chemical site—indicating a complex unit cell with multiple molecular conformations (conformers). For example, the monosolvate shows three peaks at the alcohol carbon (72-77 ppm). This site has two well-resolved peaks for the other forms.

The absence of narrow peaks for Form A and B indicates that these forms have significant conformational disorder in all parts of the unit cell. This is common for desolvate crystal forms. The peaks in the hemisolvate spectrum have both narrow and broad components. This suggests that that this particular sample was either a mixture of the hemisolvate and Form B or that there is limited disorder in the unit cell of the hemisolvate. It was difficult to control CH$_3$CN (and water) vapor pressure/humidity in the NMR sample tubes. To achieve necessary spin speed, all liquid CH$_3$CN had to be removed from the powder, and the tubes were permeable to vapor. For this reason, the samples may have had an unknown amount of CH$_3$CN and water during data acquisition. The presence of limited localized conformational disorder in Form A, Form B and the hemisolvate crystal forms was confirmed by $^{23}$Na solid-state NMR MAS spectra.

(d) Dynamic Vapor Soprtion

Acetonitrile vapor sorption isotherms were measured at 20 and 40° C. using a Surface Measurement Systems DVS-1000 gravimetric gas sorption balance. Approximately 20-30 mg of montelukast sodium Form A, or Form B, was placed on 10 the microbalance and exposed to acetonitrile vapor in nitrogen at 100 cc per min. The acetonitrile vapor pressure was ramped discretely from 0 to 95% of the saturation pressure and then back to 0%. At each pressure value, the equilibrium acetonitrile sorption was recorded. Equilibrium was defined as the point at which the sample mass was changing by less than 0.002-0.003% per min.

FIG. 3(a) shows the interconversion of monosolvate and Form A by sorption and desorption of gaseous CH$_3$CN. Beginning with Form A (with no CH$_3$CN), increasing vapor pressure gives steadily increasing sorption, with a discrete jump, indicating solvate formation, at approximately 50-60% relative pressure. During desorption, the reverse jump occurs at approximately 20%. Extrapolation of the solvate sorption data segments to 0% yields a ratio of 1.1 CH$_3$CN/montelukast sodium.

In a similar fashion, FIG. 3(b) shows the interconversion of hemisolvate and Form B by sorption and desorption of gaseous CH$_3$CN. Beginning with Form B (with no CH$_3$CN), increasing vapor pressure gives steadily increasing sorption. There is no discrete jump during sorption, however there is significant desorption hystersis, with a significant discrete loss below 5% relative pressure, which indicates prior solvate formation. Extrapolation of the solvate sorption data segments to 0% yields a ratio of 0.45 CH$_3$CN/montelukast sodium.

Form A and Form B may be considered desolvate crystal forms.

(e) Thermal Analysis

Differential scanning calorimetry (DSC) was carried out with a Mettler-Toledo DSC30 module. For dry samples, montelukast sodium was added to a 40 µl standard sealed aluminum pan with a pinhole in the lid. In all cases, approximately 3-8 mg of sample was used. Heating sequence consisted of 5° C./min heating to 100° C. [for drying and relaxation above Tg], 5° C./min cooling to 30° C., and finally, 5° C./min heating to 170° C. The melting point (onset and peak) and enthalpy of fusion were determined from the melt endotherm in the final heating scan. Glass transition temperature was taken from the midpoint of the transition. Mettler STAR$^e$ v. 6.0 software was used for data collection and analysis.

Melting traces for Form A and Form B samples consistently show a higher melting enthalpy for Form A than for Form B. Form A usually shows a melting onset temperature that is higher than that of Form B; however results are complicated by the fact that melting temperature is influenced by crystal particle size. Overall, the results suggest that Form A is more thermodynamically stable than Form B.

To assess solvate samples, montelukast powder (Form A or Form B) was added to a 7-mm stainless-steel medium-pressure pan. Excess acetonitrile was added and the pan was sealed [viton o-ring]. This procedure forms the respective solvates in situ. The heating sequence was identical as described above except that the initial drying step was skipped. Enthalpies were renormalized to montelukast mass.

Melting traces for solvate forms, as prepared, indicate that the hemisolvate is more stable than the monosolvate at all meaningful temperatures. The hemisolvate shows a melting onset temperature that is higher than that of the monosolvate. Melting enthalpies are similar. Again, it is important to note that the melting temperature can be a strong function of crystal size.

EXAMPLE 1

Preparation of Montelukast Sodium Form B

A 1000 mL thick-walled round bottom flask with an egg-shaped magnetic stir bar was charged with ~1.5 g of montelukast sodium Form A and ~400 mL of $CH_3CN$. The flask was immersed in an oil bath heated at 70° C. with a magnetic stirrer/hot plate. The temperature was monitored with a thermometer. The resulting white suspension was stirred isothermally for 4 hours. The mixture was allowed to cool to room temperature, and the solid was collected through filtration, under a stream of house nitrogen, using medium frit funnels. Form B was produced by drying the solid in air at room temperature to remove the remaining $CH_3CN$.

EXAMPLE 2

Preparation of Montelukast Sodium-acetonitrile Monosolvate [1:1 Acetonitrile:Montelukast Sodium Molar Ratio].

Method A

A 1000 mL thick-walled round bottom flask was charged with ~1.5 g montelukast sodium (Form A) and ~400 mL of $CH_3CN$. The flask was immersed in an oil bath at 50° C. for 1 to 4 hours. The mixture was allowed to cool to room temperature, and montelukast monosolvate solid was collected through filtration, under a stream of house nitrogen, using medium frit funnels.

Method B

The monosolvate was also produced by exposing Form A at room temperature to $CH_3CN$ vapor at 30 to 60%, or greater, relative $CH_3CN$ pressure as described in the vapor sorption characterization section provided hereinabove.

EXAMPLE 3

Preparation of Montelukast Sodium-acetonitrile Hemisolvate [1:2 Acetonitrile:Montelukast Sodium Molar Ratio]

Method A

A 1000 mL thick-walled round bottom flask was charged with ~1.5 g montelukast sodium (Form A) and ~400 mL of $CH_3CN$. The flask was immersed in an oil bath at 50° C. and stirred for 1 to 4 hours. The mixture was allowed to cool to room temperature, and montelukast hemisolvate solid was collected through filtration, under a stream of house nitrogen, using medium frit funnels.

Method B

The hemisolvate is also produced by exposing Form B at room temperature to $CH_3CN$ vapor at 30 to 60%, or greater, relative $CH_3CN$ pressure as described in the vapor sorption characterization section provided hereinabove.

EXAMPLE 4

Preparation of Montelukast Sodium Form A from a Mixture of Amorphous and Form A.

A mixture of amorphous and Form A montelukast sodium was suspended for a period of 24 hours in 75° C. $CH_3CN$. Stirring was limited, used to initally suspend the powder, and did not exceed one hour. The powder was then collected and acetonitrile was removed. Experimental details were similar to those previously described. The sample showed a sharpened form-A XRD pattern and increased crystallinity was proven by melting enthalpy, which increased from 15.7 J/g to 28.7 J/g. The annealed sample appeared to have a crystalline content that was close to 100%. Enthalpies of 29 (+/-2) J/g have been obtained for Form-A samples that appear substantially free of amorphous or other phases.

What is claimed is:

1. Form B montelukast sodium characterized as having an x-ray powder diffraction pattern peak position substantially as shown:

| 2 θ | d spacing (Å) | Intensity |
|---|---|---|
| 5.4 | 16.4 | s |
| 5.7 | 15.6 | vs |
| 9.5 | 9.3 | m |
| 10.4 | 8.5 | m |
| 17.1 | 5.2 | s |
| 18.7 | 4.73 | s |
| 21.6 | 4.11 | s. |

2. Montelukast sodium:acetonitrile monosolvate.

3. Montelukast sodium:acetonitrile monosolvate of claim 2 characterized by having $^{13}C$ solid-state CPMAS NMR chemical shifts in ppm at 72 (sharp triplet), 74 (sharp triplet), 77 (sharp triplet), 179 (sharp doublet), and 182 (sharp doublet).

4. Montelukast sodium:acetonitrile monosolvate of claim 2 further characterized by having X-ray powder diffraction peaks substantially as shown:

| 2 θ | d spacing (Å) | Intensity |
|---|---|---|
| 4.30 | 20.5 | vs |
| 5.9 | 14.9 | s |
| 6.2 | 14.3 | s |
| 6.8 | 13.0 | w |
| 7.3 | 12.0 | w |
| 10.5 | 8.4 | m |
| 11.0 | 8.0 | w |
| 12.7 | 7.0 | m |
| 16.2 | 5.5 | s |
| 18.1 | 4.90 | w |
| 18.7 | 4.74 | w |
| 21.6 | 4.12 | w |
| 23.4 | 3.80 | w |
| 23.9 | 3.72 | w. |

5. Montelukast sodium:acetonitrile hemisolvate.

6. Montelukast sodium:acetonitrile hemisolvate of claim 4 characterized by having $^{13}$C solid-state CPMAS NMR chemical shifts in ppm at 27 (well resolved) and 55 (well resolved), referenced by setting the carbonyl resonance of glycine to 176.08.

7. Montelukast sodium:acetonitrile hemisolvate of claim 4 characterized by having X-ray powder diffraction peaks substantially as shown:

| 2θ | d spacing (Å) | Intensity |
|---|---|---|
| 4.57 | 19.3 | s |
| 5.3 | 16.7 | s |
| 5.6 | 15.7 | vs |
| 6.5 | 13.6 | m |
| 9.4 | 9.4 | m |
| 10.3 | 8.6 | w |
| 11.6 | 7.6 | m |
| 14.1 | 6.3 | w |
| 14.5 | 6.1 | m |
| 15.1 | 5.8 | w |
| 16.2 | 5.5 | m |
| 17.0 | 5.2 | m |
| 18.5 | 4.79 | s |

-continued

| 2θ | d spacing (Å) | Intensity |
|---|---|---|
| 20.8 | 4.26 | m |
| 21.3 | 4.17 | s. |

8. A method for the preparation of montelukast sodium Form A substantially free of amorphous montelukast sodium comprising: 1) collecting montelukast sodium:acetonitrile monosolvate; and 2) removing acetonitrile from the collected monosolvate.

9. A method for the preparation of montelukast sodium Form A substantially free of amorphous montelukast sodium comprising: 1) contacting amorphous montelukast sodium or a mixture of amorphous montelukast sodium and montelukast sodium Form A with acetonitrile to form montelukast sodium:acetonitrile monosolvate; 2) collecting said monosolvate; and 3) removing acetonitrile from the collected monosolvate.

10. The method of claim 8 wherein a mixture of amorphous montelukast sodium and montelukast sodium Form A is used in step 1).

* * * * *